United States Patent [19]

Pfahl et al.

[11] Patent Number: 5,183,736
[45] Date of Patent: Feb. 2, 1993

[54] METHODS USING ESTROGEN RECEPTOR AS A CONSTITUTIVE TRANSCRIPTIONAL ACTIVATOR AND A REPRESSOR

[75] Inventors: Magnus Pfahl, Solana Beach; Maty Tzukerman, San Diego, both of Calif.

[73] Assignee: La Jolla Cancer Research Foundation, La Jolla, Calif.

[21] Appl. No.: 502,325

[22] Filed: Mar. 30, 1990

[51] Int. Cl.$^5$ .............................................. C12Q 1/68
[52] U.S. Cl. ...................................... 435/6; 456/501; 435/7.1; 435/7.8
[58] Field of Search .............................. 436/501–504, 436/510, 813, 817; 435/6, 7.1, 7.8

[56] References Cited

U.S. PATENT DOCUMENTS 4,711,856 12/1987 Spelsberg ............................ 436/504
4,806,464 2/1989 Spelsberg ................................ 435/6

OTHER PUBLICATIONS

Mathews et al.: Analytical Strategies for the Use of DNA Probes, Analytical Biochemistry 169, 1–25, Feb. 1988.

Primary Examiner—Christine M. Nucker
Assistant Examiner—Jeffrey Stucker
Attorney, Agent, or Firm—Needle & Rosenberg

[57] ABSTRACT

The invention provides the discovery that estrogen receptor is a constitutive transcriptional activator and a repressor. These activities are lacking in the mutant estrogen receptor. The invention provides assays and methods for determining estrogen binding activity of ligands. The invention also provides therapeutic methods and the detection of pathologies associated with a mutated estrogen receptor.

17 Claims, 14 Drawing Sheets

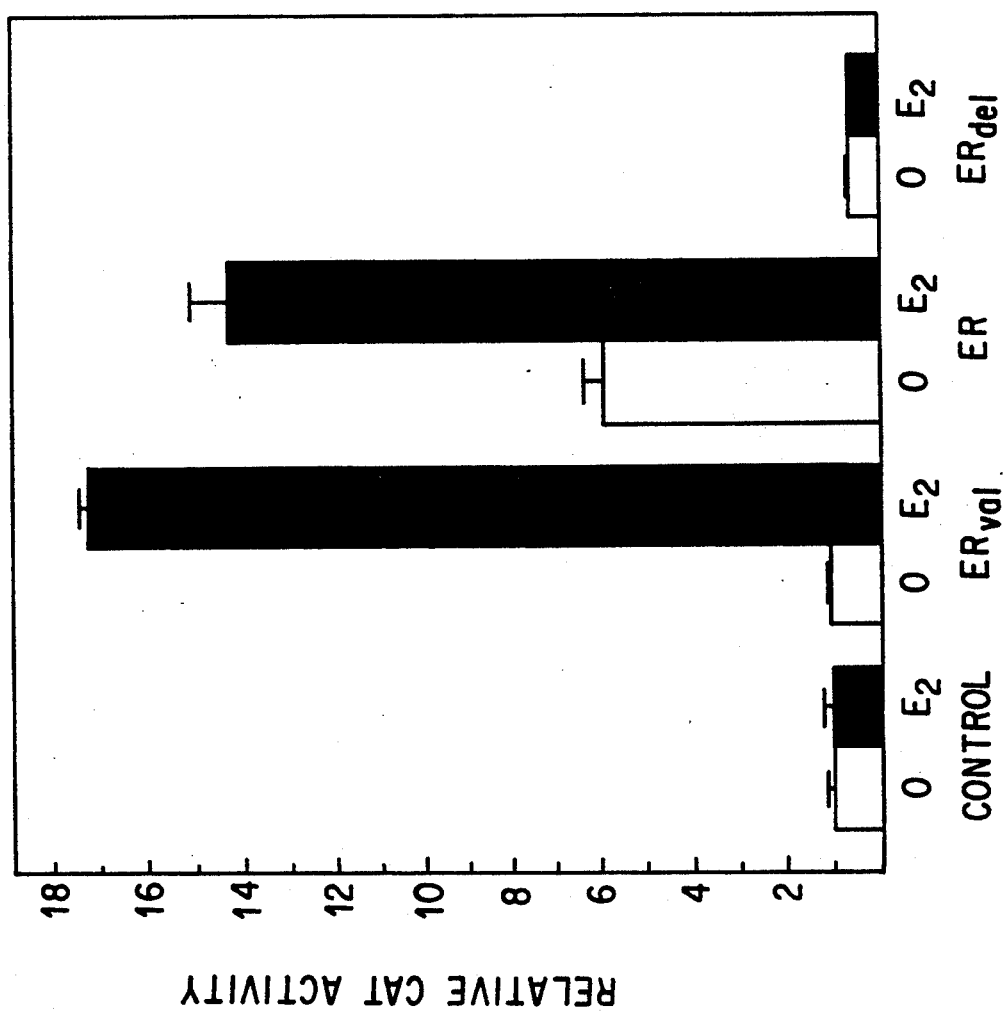

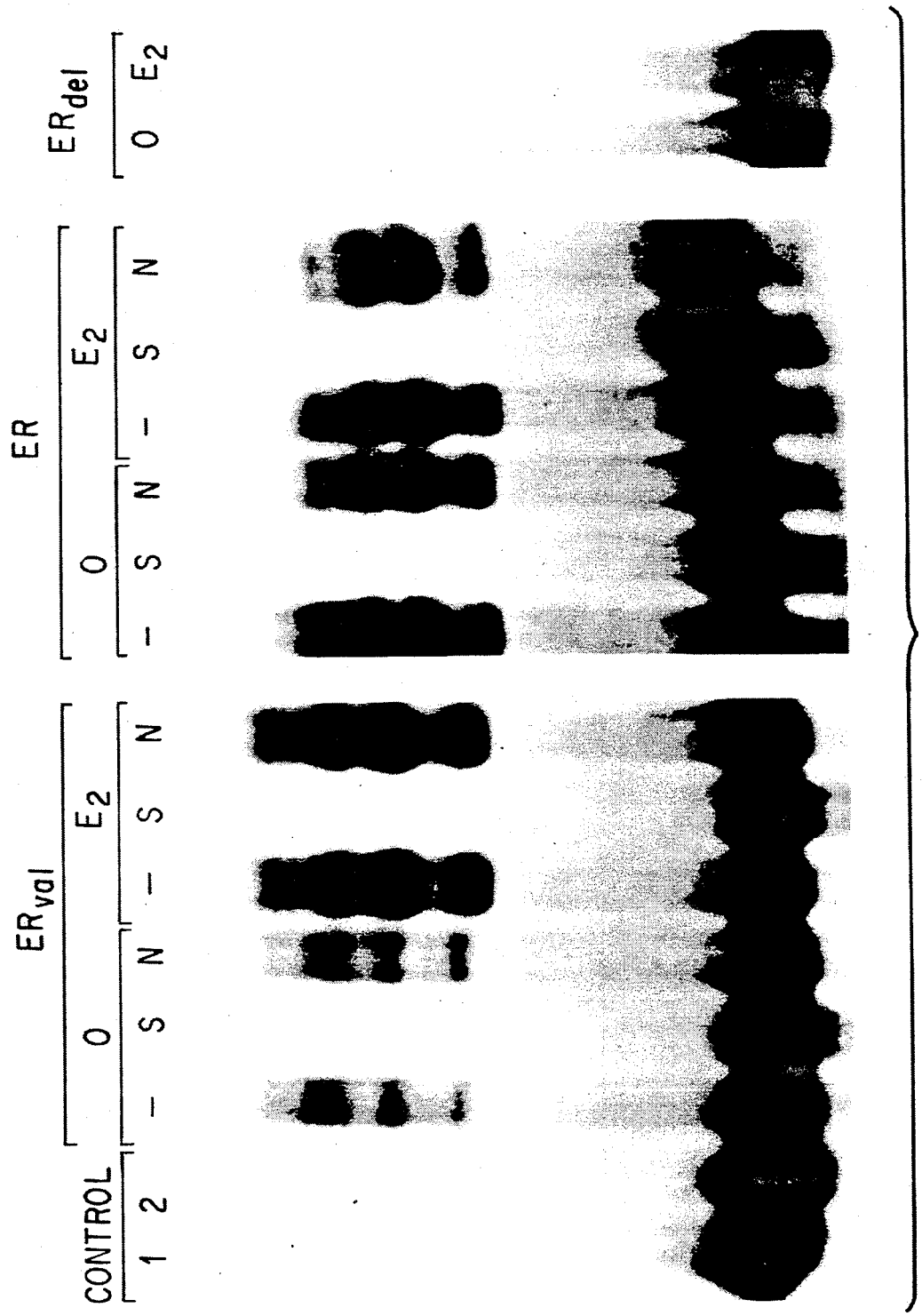

METHODS USING ESTROGEN RECEPTOR AS A CONSTITUTIVE TRANSCRIPTIONAL ACTIVATOR AND A REPRESSOR

This invention was funded in part by NIH Grant DK 35083. The United States government has rights in the invention.

BACKGROUND OF THE INVENTION

This invention relates to hormone receptors and, more particularly, to methods of altering the activity of estrogen receptors.

Throughout this application various publications are referenced by superscript numbers. Full citations for these publications may be found at the end of the specification immediately preceding the claims. The disclosures of these publications in their entireties are hereby incorporated by reference into this application in order to more fully describe the state of the art to which this invention pertains.

Gene regulatory proteins are essential for cell regulation. A well studied family of gene regulatory proteins is the large steroid hormone receptor family. These receptor proteins enable cells to respond to various lipid-soluble hormones by activating or repressing specific genes. They possess a central DNA-binding domain of about 100 amino acids. For some members of this family, a transcription-activating domain has been located in an amino-terminal region. In addition, these receptors all contain a specific hormone-binding domain in the carboxylterminal part of the protein. One member of this family is the estrogen receptor (ER). Like the other members of the steroid-hormone receptor family, estrogen receptors are activated by the binding of a small signaling molecule to a separate ligand-binding domain.

The conventional model for steroid hormone action has assumed that steroid hormone receptors act as transcriptional regulators only when complexed with their ligands. It has, however, become evident that most types of steroid receptors are present in the cell nucleus even in the absence of ligand[1-3]. At present, the only exception to this appears to be the glucocorticoid receptor[1,4]. The presence of the receptors in the nucleus, even in the absence of hormone, suggest possible additional regulatory functions for the unliganded state. We have recently found that other members of the nuclear receptor family, the thyroid hormone receptors (TR), have a dual regulatory role: in the presence of hormone they function as transcriptional activators whereas in the absence of hormone they are response element specific transcriptional repressors[5]. The estrogen receptor is structurally related to the TR[6-8] and can also activate thyroid hormone responsive elements (TRE).

Despite these similarities, it has long been established that the estrogen receptor acts in the conventional model for steroid hormone action by acting as transcriptional regulators only when complexed to estrogen. The present invention provides, contrary to this universally believed principle, that ER does not require estrogen to act as a transcriptional regulator. Therefore, the invention provides the surprising discovery that estrogen receptor has a constitutive activator and a repressor activity in the absence of estrogen. Also provided is the discovery that mutant estrogen receptors lack this constitutive activator and the repressor activity in the absence of estrogen. Since many pathologies, for example breast cancer, are associated with estrogen, the invention satisfies a long felt need by providing methods of controlling these pathologies and screening ligands which are useful in treating the pathologies.

SUMMARY OF THE INVENTION

The invention provides the discovery that estrogen receptor is a constitutive transcriptional activator and a repressor. These activities are lacking in the mutant estrogen receptor. The invention provides assays and methods for determining estrogen binding activity of ligands. The invention also provides therapeutic methods and the detection of pathologies associated with a mutated estrogen receptor.

(a) Induction of CAT activity. CV-1 cells were transiently cotransfected with 2 μg of ERE-CAT reporter plasmid alone (control) or together with 1 μg of receptor expression vector and 3 μg of β-gal expression vector (pCH110, Pharmacia) which served as an internal control. Carrier DNA (Bluescript) was added to 23 μg total DNA. Cultures were treated with hormones as indicated ($10^{-8}$M $E_2$, $10^{-7}$M $T_3$, $6\times10^{-7}$M RA) and assayed for CAT enzyme activity. CAT activity is corrected for β-gal activity.

(b) ER constitutive transcription activity depends on the ER/ERE ratio. CV-1 cells were cotransfected with 2 μg ERE reporter plasmid alone (control) and with decreasing amounts of ER expression vector as indicated. The level of CAT transcription activity was measured in the absence, and in the presence of $10M^{-8}$ $E_2$ or $10^{-8}$ M OH-Tam (OHT) or both, as indicated. A representative experiment is shown.

(c,d) $E_2$ dependent transcriptional activation of ER and $ER_{val}$. Titrations of the $E_2$ response were carried out using a transient cotransfection assay. CV-1 cells were cotransfected as described under (a) using ER (c) or $ER_{val}$ (d) expression vectors and reporter plasmid. Cultures were incubated with varying concentrations of $E_2$ as indicated.

FIG. 2 shows in vitro DNA binding of ER and mutant ER.

(a) DNA binding of ER and ER mutants. ER, $ER_{val}$, and $ER_{del}$ proteins were synthesized in vitro, and incubated with $^{32}$p-labelled ERE in the presence ($E_2$) and absence (O) of $10M^{-8}$ oestradiol. As control, the labelled ERE (lane 1) and the lysate (lane 2) were run alone. Binding of receptors to labelled ERE was competed with 50 fold excess of unlabelled ERE(S) or nonspecific unlabelled oligonucleotides (N).

(b) Effect of Tamoxifen on DNA binding of ER and $ER_{val}$. ER and $ER_{val}$ in vitro synthesized proteins were incubated with $^{32}$P-labelled ERE in the absence (O) or in the presence of $10^{-8}$M estradiol ($E_2$) or $4\times10^{-7}$M Tamoxifen (Tam), as indicated.

FIG. 3 shows the effect of antiestrogen on transcriptional activity of ER and $ER_{val}$.

(a) Effect of 4-hydroxytamoxifen on ER and $ER_{val}$ activity. CV-1 cells were transiently cotransfected with ER or $ER_{val}$ expression vectors and reporter plasmid as described in FIG. 1. Cells were incubated in the absence (O) or in the presence of $10^{-8}$M $E_2$, and 4-hydroxytamoxifen (OH-Tam) as indicated. CAT enzyme activities presented are corrected for transfection efficiency by measuring β-gal expression.

(b,c) Effect of OH-Tam on hormonal induction of ER. Titrations of induction of ER by $E_2$ were performed in the presence of constant amounts of OH-Tam. CV-1 cells were cotransfected as described above. 24 h after transfection cultures were treated with increasing concentration of $E_2$ as indicated and constant amounts of OH-Tam $10^{-9}M$ (b) or $10^{-8}M$ (c). CAT activities were measured as described.

Figure 4A:
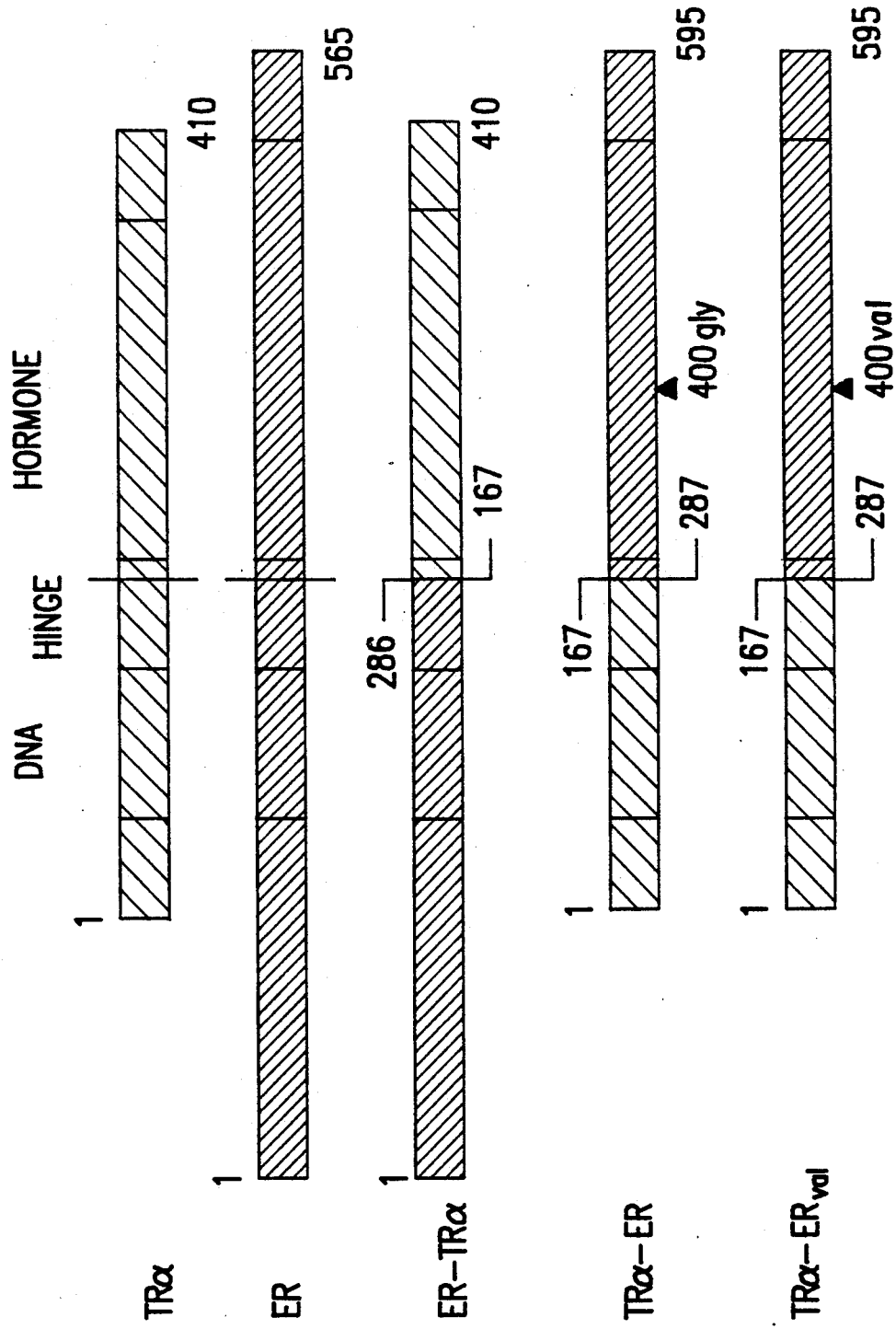

FIG. 4 shows the hybrid receptor analysis.

(a) Construction of hybrid receptors. Hybrid receptors TRα-ER and TRα-ER$_{val}$ contain amino acid 1-166 of the human TRα receptor which includes the DNA binding domain up to the hinge region, and amino acids 287-595 of ER or ER$_{val}$ which includes a portion of the hinge region and the hormone binding domain. The ER-TRα hybrid receptor contains amino acid 1-286 of ER which includes the DNA binding domain up to the hinge region, and amino acids 266-410 of TRα which includes a portion of the hinge region and the TRα hormone binding domain.

Figure 1B:
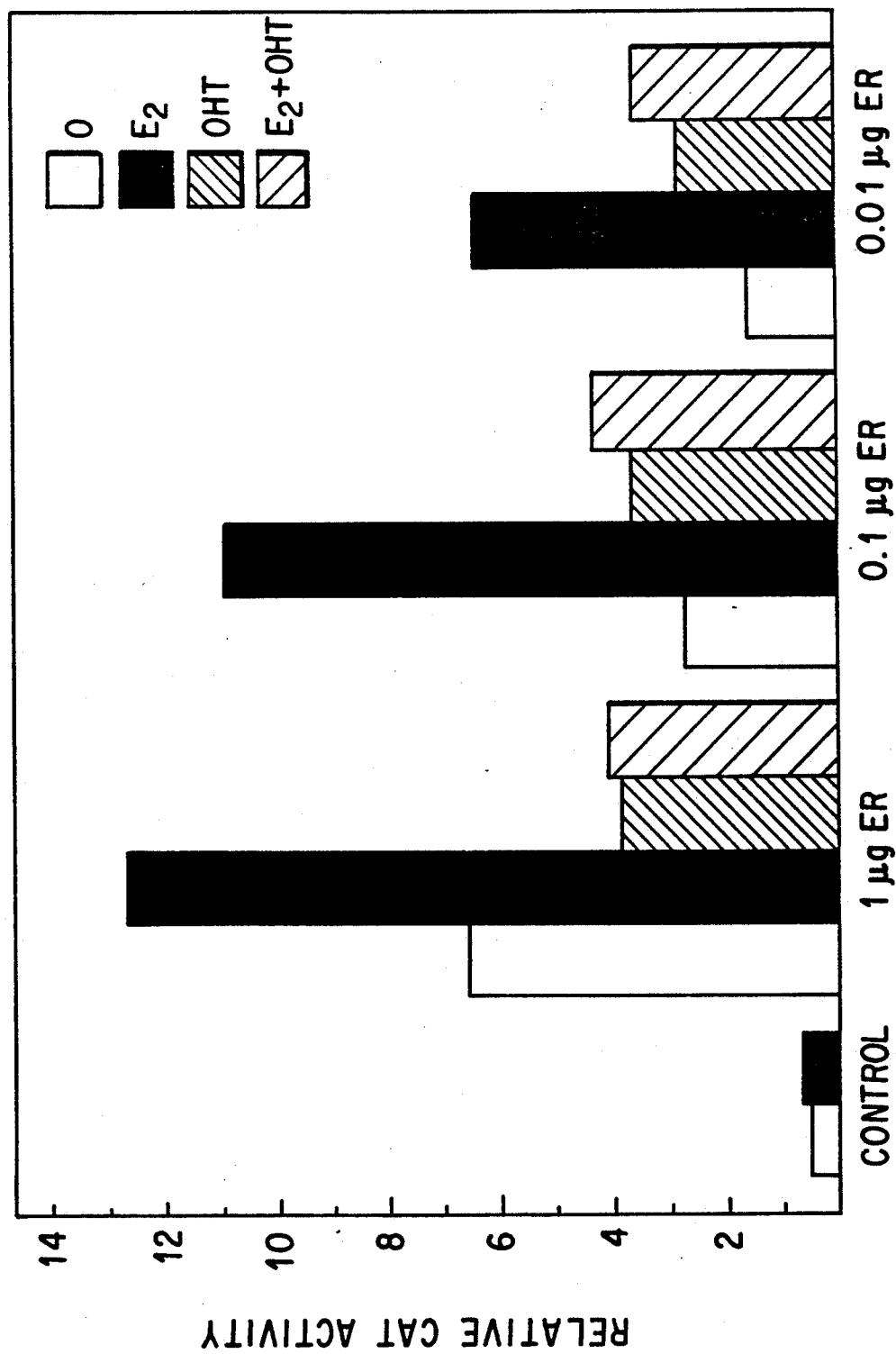
FIG. 1 shows activation of transcription of wild type and mutants ERs.
Figure 1C:
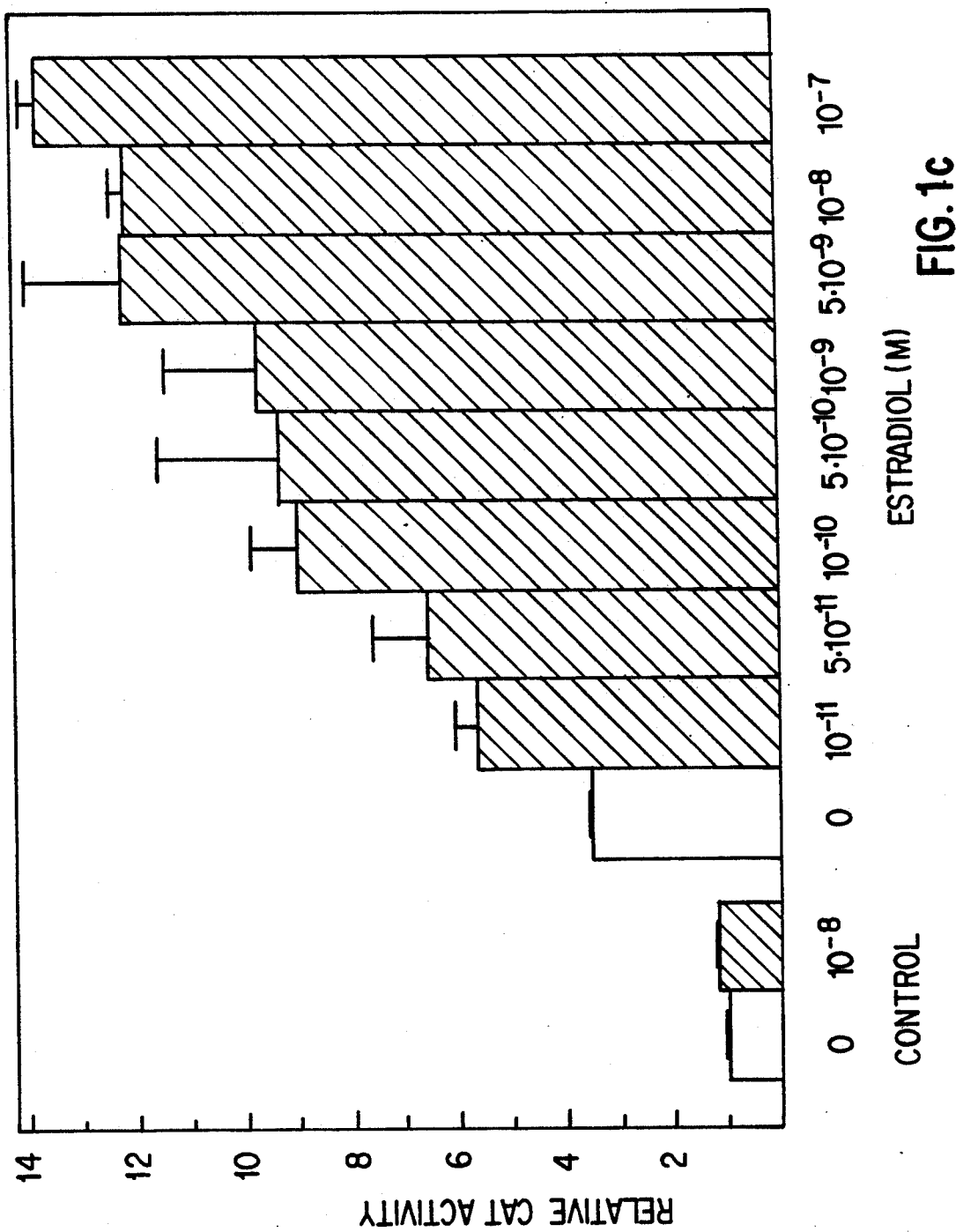
Figure 1D:
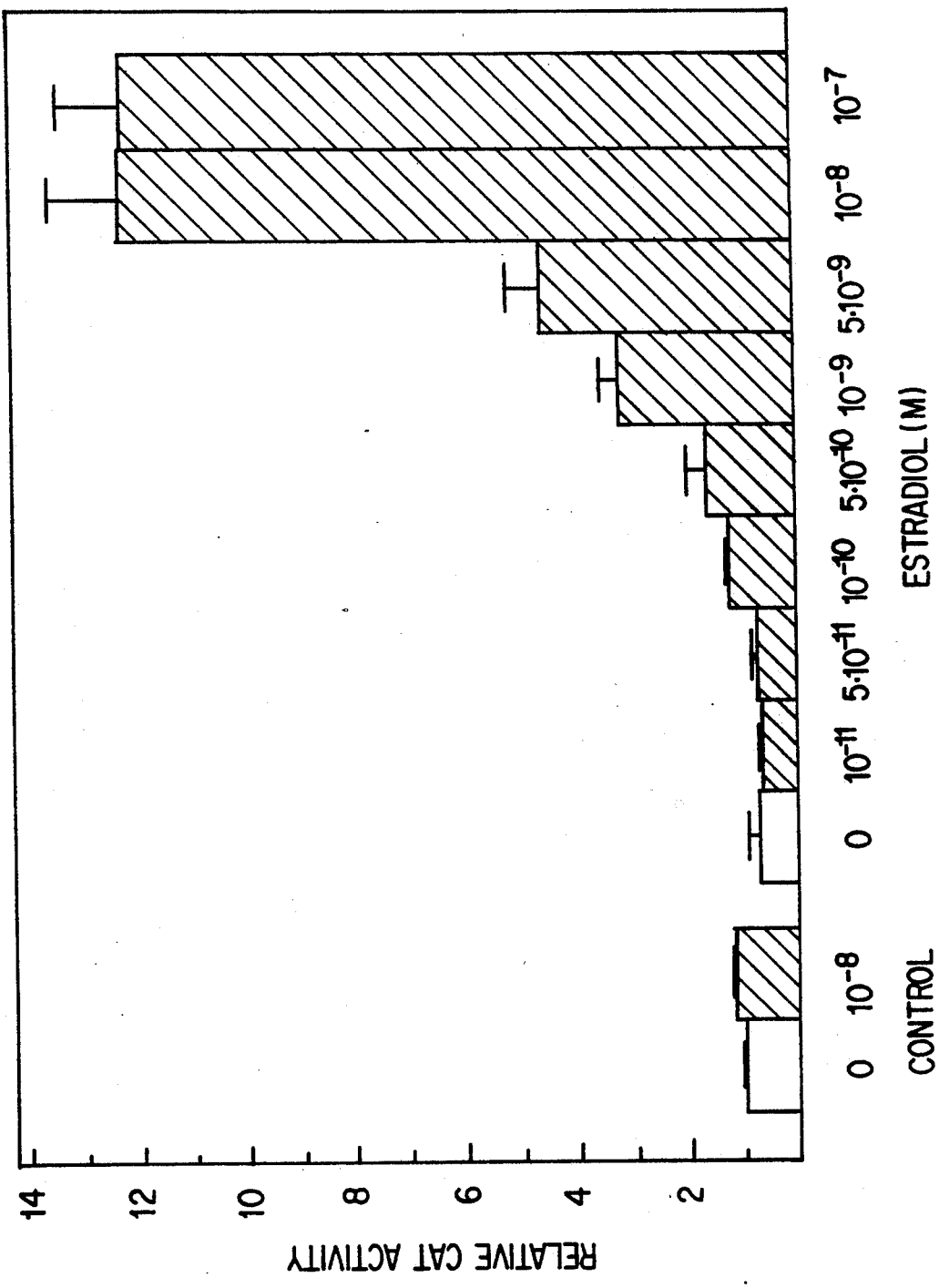

(b) CV-1 cells were cotransfected with TRα expression vector, or TRα-ER expression vector and TRE-tk-CAT reporter plasmid as described in FIG. 1. Cultures were maintained in the absence of hormone (O) or in the presence of hormone ($10^{-8}M$ $E_2$; $10^{-7}M$ $T_3$) as indicated. Cells were collected and CAT activities were assayed as described. A representative experiment is shown.

(c) DNA binding of the hybrid receptors. TRα-ER, TRα-ER$_{val}$, and ER-TRα were synthesized in vitro. Proteins were incubated with the labelled responsive elements ERE or TRE. Hormones were added to the reaction mixtures as indicated ($10^{-7}M$ $T_3$, $10^{-8}M$ $E_2$). DNA binding was analyzed as described in FIG. 2. The bands observed could in all cases be competed with a fifty-fold excess of unlabelled response element, but not with nonspecific DNA.

Figure 5:
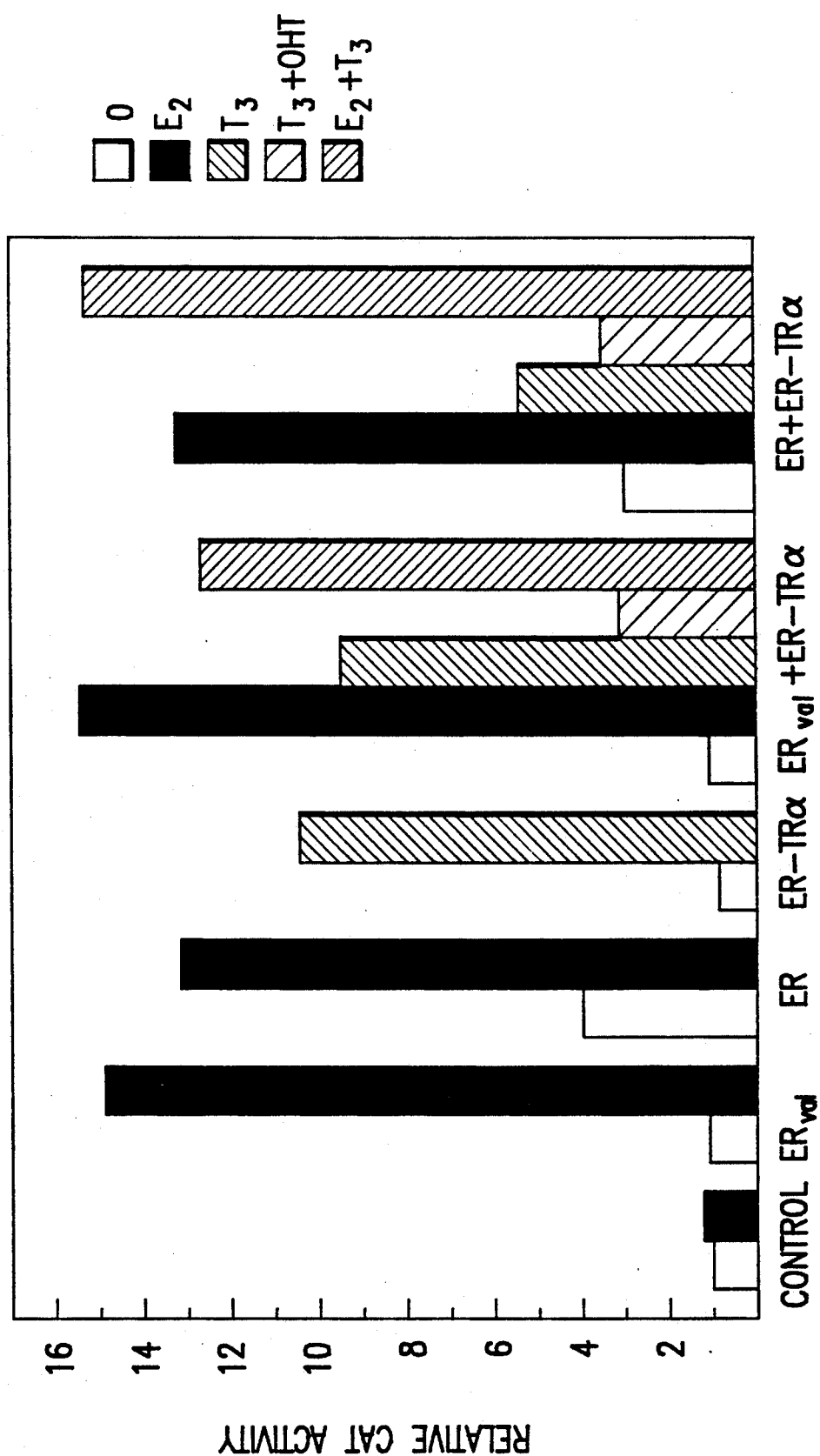

FIG. 5 shows repressor activity of ER. CV-1 cells were cotransfected with 1 μg ER or ER$_{val}$ expression vector, 0.5 μg ER-TRα expression vector and 2 μg of ERE-CAT reporter plasmid. 24 h after transfection hormones were added as indicated: $10^{-8}M$ $E_2$; $10^{-7}M$ $T_3$; $10^{-8}M$ OH-Tam. CAT activities were measured as described in the Example. A representative experiment is shown.

Figure 6:
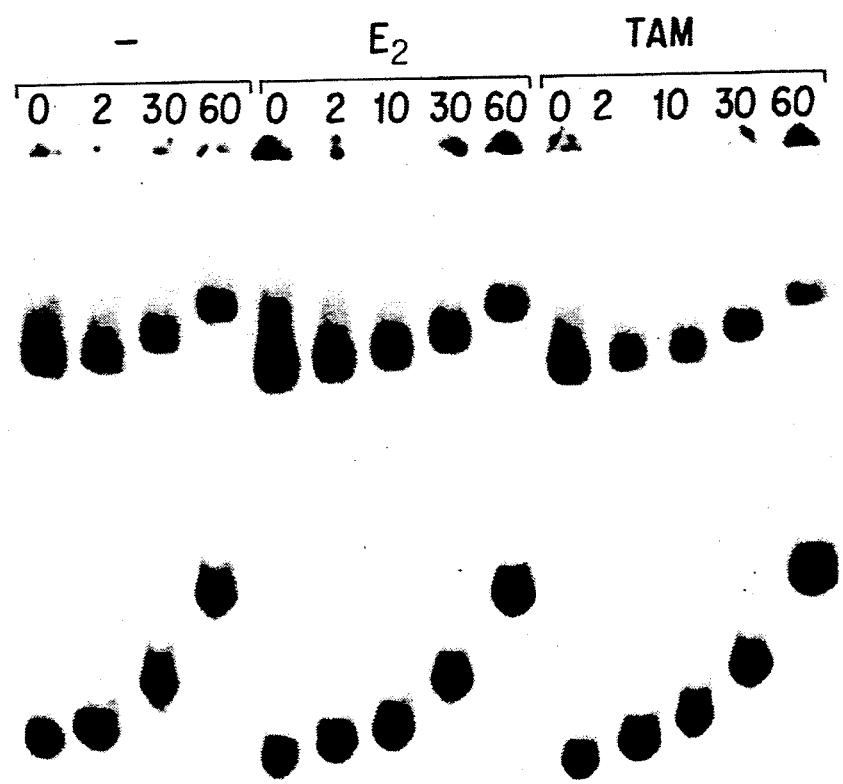

FIG. 6 shows the effect of $E_2$ and OH-Tam on the stability of ER-ERE complex. In vitro synthesized ER protein was incubated at 25° C. for 20 min with $^{32}P$-labelled ERE in the absence of hormone, in the presence of $10^{-8}M$ $E_2$, or in the presence of $10^{-8}M$ OH-Tam. At time 0, a 50 fold excess of non-labelled ERE was added. After incubation at 10° C. for the indicated time intervals, aliquots were loaded on a running non-denaturing 5% polyacrylamide gel.

DETAILED DESCRIPTION OF THE INVENTION

As used herein, "estrogen activity" means the ability to bind an estrogen receptor and enhance the transcription promoting activity of the estrogen receptor. Many estrogens have this activity, e.g. estradiol. The activity can readily be determined using the methods set forth in the Example.

As used herein, "antiestrogen activity" means the ability to interfere with the binding of estrogen to its receptor and thus reduce or prevent the transcriptional promoting activity of the estrogen receptor.

As used herein "basal level expression" means the expression resulting from the constitutive activity of estrogen receptor in the substantial absence of estrogen.

As used herein "mutated estrogen receptor" (or "mutant estrogen receptor") means any mutation in the wild type estrogen receptor which substantially terminates basal level expression but does not prevent estrogen activity or which terminates repressor function. In particular, certain amino acid substitutions at position 400 of the estrogen receptor exhibit such altered activity. One example of a mutated estrogen receptor is "ER$_{val}$" which has valine instead of the normal glycine at amino acid position 400. Another example is ER$_{Met}$ which has methionine at position 400. Other mutated receptors could be made, for example, by site directed mutagenesis and expressed by well-known methods. Such a mutated receptor could be tested for activity as set forth in the Example. Other mutant receptors that have deletions in the ligand binding domain can substantially terminate the repressor function of the receptor. An example is ER$_{DEL}$, described below.

As used herein "estrogen receptor associated pathology" means any pathology which results from a mutant estrogen receptor. Examples of such pathologies can include a cancer, such as breast cancer, and osteoporosis. The methods described herein are effective for any such pathology, even if there is currently no known association between the pathology and a mutated estrogen receptor. The method described herein also provides a means to determine the association of a pathology and a mutated estrogen receptor.

As used herein "repressor activity" means the ability of estrogen receptor to bind DNA, for example at the estrogen responsive element (ERE), and either (1) block other transcriptional activators, which would bind a portion of the ERE, from binding or (2) block or prevent other transcriptional activators from exerting their activity.

As used herein, "substantial absence of estrogen" means estrogen is not present in sufficient levels to promote significant estrogen activity. Therefore, in the "substantial absence of estrogen" basal level expression of estrogen receptor dominates the expression of "estrogen receptor responsive genes". "Estrogen receptor responsive genes" means those genes which are transcriptionally activated by an estrogen receptor.

As used herein, "therapeutic amount" means the amount necessary to treat a pathology. This amount can vary depending on many factors, e.g. the size of the subject or severity of the condition. Optimal therapeutic amounts can be determined using standard methods.

The invention provides a method of comparatively determining estrogen or antiestrogen activity of a ligand for an estrogen receptor comprising separately binding the ligand to the estrogen receptor and a mutated estrogen receptor, comparing the effect of the ligand on the activity of the estrogen receptor and the mutated estrogen receptor, thereby comparatively determining estrogen or antiestrogen activity of a ligand for an estrogen receptor. The comparison of the effect of the ligand on the activity of the estrogen receptor can be determined, for example, by a gel retardation assay or transient transfection.

Also provided is a method of selecting a ligand which increases or decreases the basal level transcription of a mutated estrogen receptor. The method comprises the steps of contacting the ligand with the mutated estrogen receptor, determining the effect of the ligand on basal level transcription, and selecting those ligands which either increase or decrease the basal level transcription.

A method of selecting a ligand for increasing or decreasing the activity of a mutated estrogen receptor compared to an estrogen receptor is also provided. The method comprises the steps of separately contacting a mutated estrogen receptor and the estrogen receptor with the ligand, comparing the effect of the ligand on the activity of the mutated estrogen receptor and the estrogen receptor, and selecting those ligands which increase or decrease the mutated estrogen receptor activity more than the estrogen receptor activity.

A method of diagnosing or predicting the predisposition to an estrogen receptor associated pathology in an individual is provided. The method comprises detecting mutant estrogen receptors, the presence of mutant estrogen receptors indicates the pathology or a predisposition to the pathology. The mutant receptor can be detected by several methods. One preferred method is by contacting a nucleotide probe having a sequence complementary to the nucleic acid sequence of the mutated estrogen receptor with a nucleic acid containing sample from the individual under conditions such that substantially only nucleic acid sequences of the mutated estrogen receptor will hybridize with the probe, and detecting the nucleic acids which hybridize, thereby detecting a mutant estrogen receptor. An additional method is detecting the mutant receptor with a specific ligand, such as an antibody. The pathology detected can result from a defect in the repressor activity of the estrogen receptor. An example of such a pathology is a cancer, especially breast cancer. Alternatively, the pathology can result from a defect in the basal level transcription activity of the estrogen receptor. An example of this pathology is osteoporosis.

The invention also provides a method of promoting basal level transcription of a nucleic acid which is activated by estrogen receptor in the presence of estrogen comprising adding estrogen receptor or a compound having estrogen receptor activity to the nucleic acid in the substantial absence of estrogen.

The invention further provides a method of inhibiting basal level transcription of a nucleic acid which is activated by estrogen receptor in the presence of estrogen comprising preventing the attachment of the estrogen receptor to DNA in the substantial absence of estrogen. The attachment of the estrogen receptor to DNA can be prevented by binding the estrogen receptor or the DNA with a ligand. In the normal course the DNA is the estrogen responsive element.

The invention still further provides a method of inhibiting the activation of transcription by DNA binding receptors which can activate transcription and which are blocked by the binding of the estrogen receptor to DNA. The method comprises adding estrogen receptor or a compound having estrogen receptor activity to the nucleic acid in the substantial absence of estrogen so as to allow the estrogen receptor to bind the DNA.

The invention also provides a method of treating a pathology in a subject resulting from a mutant estrogen receptor comprising administering a therapeutic amount of estrogen receptor to the subject so as to increase or restore the basal level transcription of estrogen receptor responsive genes. An example of such a pathology is osteoporosis.

A method of treating a pathology in a subject resulting from a mutant estrogen receptor is provided. The method comprises administering a therapeutic amount of estrogen receptor to the subject so as to repress non-estrogen receptor transcription activation. In one embodiment, the non-estrogen receptor transcription activation is repressed by estrogen receptor binding to DNA which would be bound by the non-estrogen receptor in the absence of estrogen receptor. In an alternative embodiment, the non-estrogen receptor transcription activation is repressed by estrogen receptor binding to DNA and blocking the transcription effect of the non-estrogen receptor. An example of a pathology treated by this method is a cancer.

The invention further provides a method of treating a pathology in a subject expressing a mutant estrogen receptor comprising administering a therapeutic amount of a ligand which binds the mutant receptor and changes the receptor conformation to allow binding to DNA so as to increase or restore the basal level transcription of estrogen receptor responsive genes. In one embodiment the pathology is osteoporosis. Ligands effective in the method include tamoxifen and 4-hydroxytamoxifen. The mutation can be in the ligand binding domain of the estrogen receptor.

Finally, the invention provides a method of treating a pathology in a subject expressing a mutant estrogen receptor comprising administering a therapeutic amount of a ligand which binds the mutant receptor and changes the receptor conformation to allow binding to DNA so as to repress the activity of other transcriptional activators. One pathology treated by this method is a cancer. Effective ligands include tamoxifen and 4-hydroxytamoxifen. In one embodiment the mutation is in the ligand binding domain of the estrogen receptor.

The results of the invention show that the wild type human ER has an intrinsic transcriptional enhancing activity in the absence of the estrogen estradiol ($E_2$). One possible argument against this interpretation is that trace amounts of estrogen or estrogen-like activities were present in both the in vitro synthesized receptor preparations and in the tissue culture medium used. However, these estrogens would have to be present at very low concentrations (below $10^{-11}M$, as judged from the induction curve FIG. 1c). Such low concentrations are not known to be of physiological significance. For example, serum levels of estradiol for human males range between 3 and $18 \times 10^{-11}M$ and for postmenopausal females, between 3 and $15 \times 10^{-11}M$[12]. When one considers the ER as an allosteric protein whose activation function is stabilized by agonists, then our results suggests that in the absence of ligand a considerable portion of the ER molecules are already in the activation conformation. Our data on the ER represents the first example of a nuclear receptor that has constitutive activity.

Figure 3A:
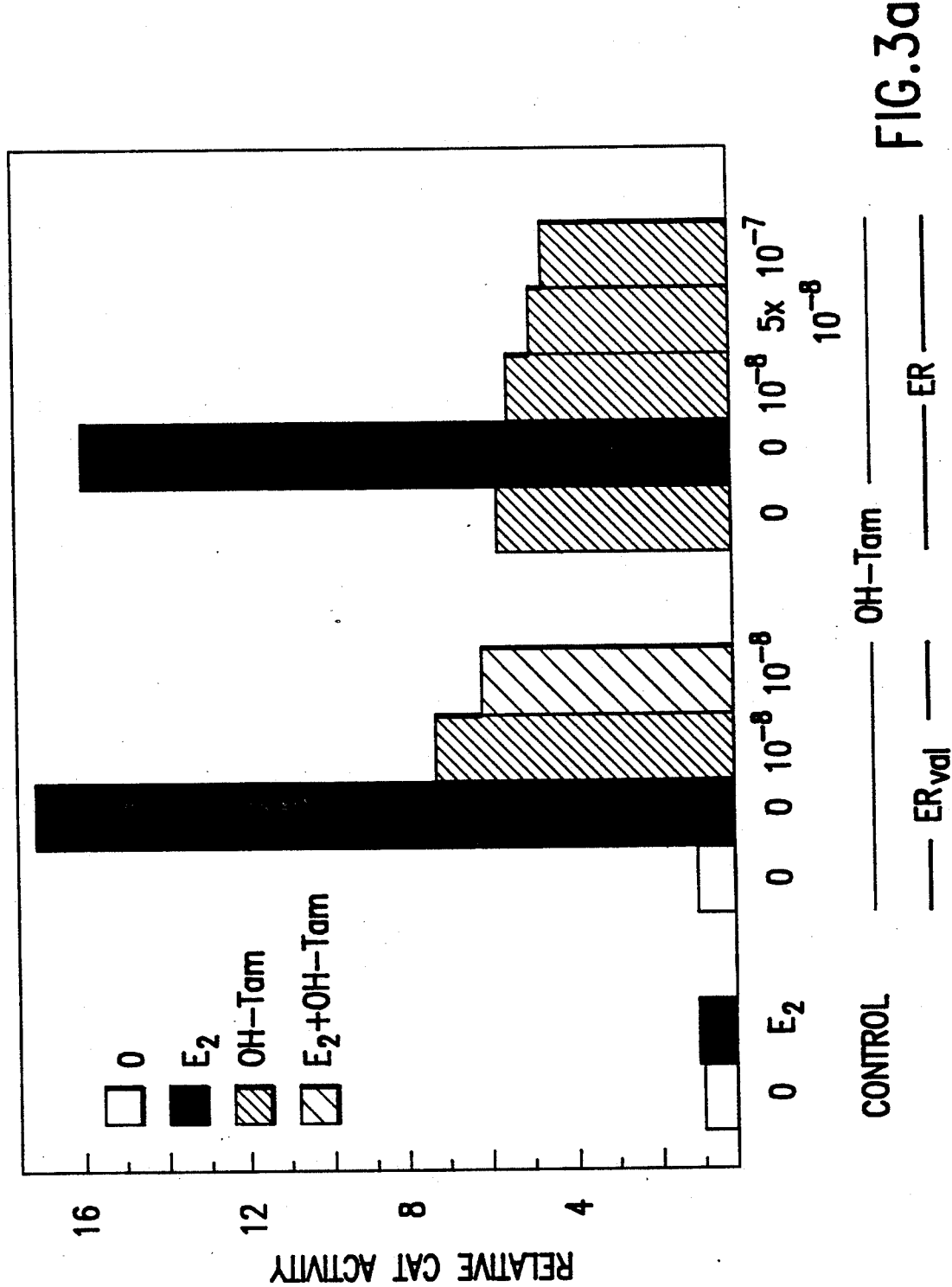
Figure 3B:
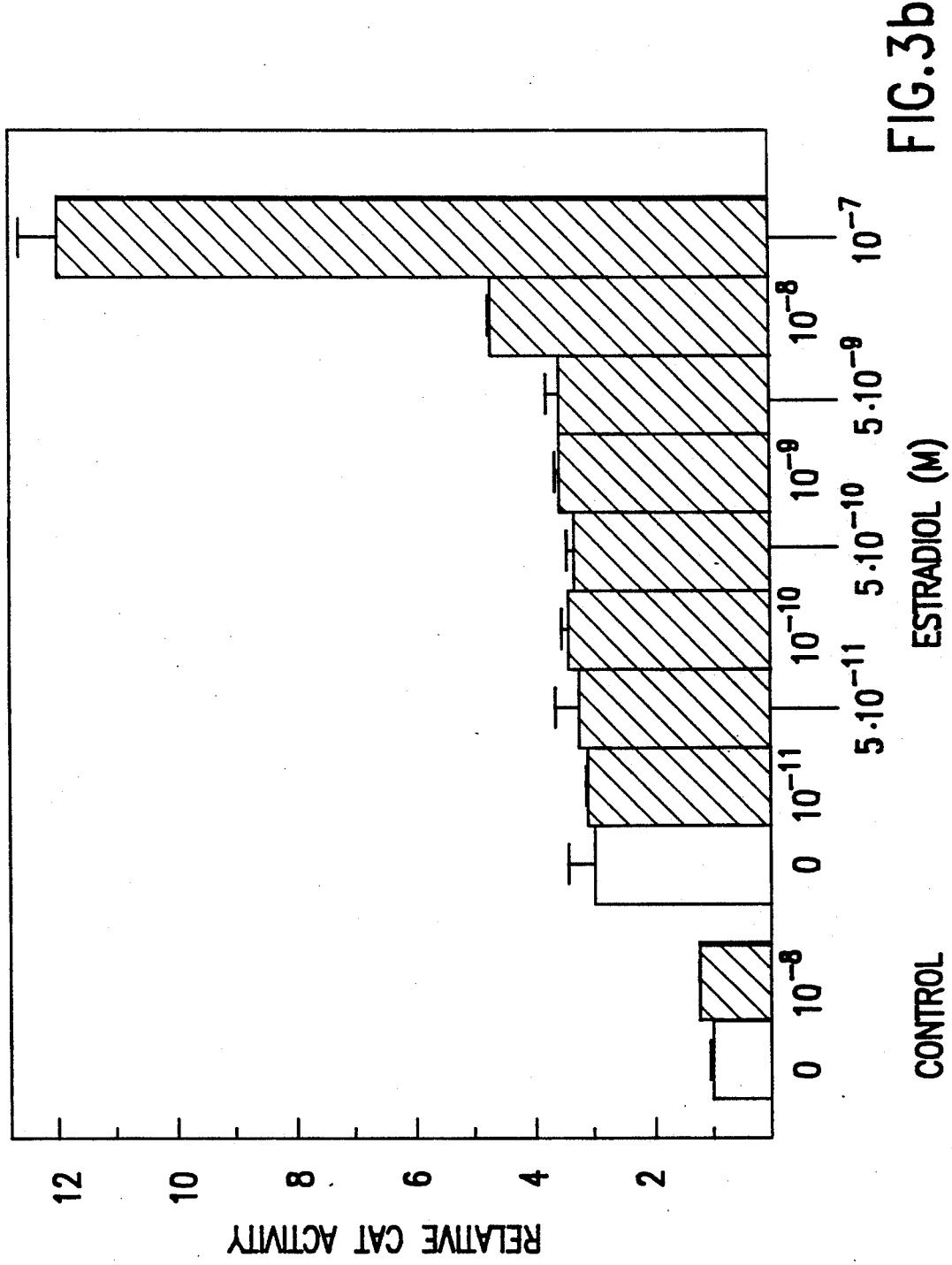

Overall, ER clearly does not function according to the classical model for steroid hormone action, which predicts that all receptor functions are ligand dependent. ER has multiple functions: In the absence of agonist it functions as an intermediate transcriptional activator that because of its high affinity, can also prevent access of other low affinity transcriptional activators from inducing an estrogen responsive element (ERE). Estrodiol ($E_2$), even at very low levels, induces a concentration dependent increase in the ER activity. In the presence of an antagonist, the ER repressing activity dominates and the activation capacity of other transcriptional activators is decreased to the constitutive basal level. The constitutive activity of ER is to some extent dependent on the ER to ERE ratio. At very low ER concentrations antiestrogens enhance ER activation of gene transcription (FIG. 1b). However, hydroxytamoxifen (OH-Tam) or tamoxifen (Tam) do not appear to function as classical weak agonists since the agonist effect does not increase with increasing concentrations of ligand (FIG. 3a). OH-Tam, therefore, appears to stabilize ER (as it does with ER$_{val}$), facilitate dimerization, or favor ER-DNA associations.

The mutant receptor ER$_{val}$ lacks both the constitutive activation and the repressor function of wild type ER. E$_2$ restores its activation capacity. The antiestrogen OH-Tam restores the ability of ER$_{val}$ to repress and simultaneously restores the basal gene activation capacity. These results demonstrate that the GLY at position 400 fulfills an important role and may contribute to the overall structural stability of the ER hormone binding domain. The functions of the ER$_{val}$ ligand binding domain apparently can be stabilized by ligand interaction.

The VAL-400 mutant was cloned from the human mammary carcinoma cell line MCF7. The mutation could have contributed to the progression of the tumor. The above model predicts that individuals carrying an ER$_{val}$ mutant or another similar mutation would have an increased dependence on estrogen for their estrogen receptor function. In the case of homozygosity, an even stronger estrogen dependence for ER function would be expected. Female carriers of these mutations can be affected by increased bone fragility after menopause.

The repressor function of ER can be useful in preventing nonspecific activation of E$_2$ responsive genes. A lack of this function can contribute to uncontrolled gene activation and cancer progression. Since such receptors have lost repressor function, an increased level of gene expression can result and this can lead to increased proliferation especially when estrogen levels are low, for example after menopause.

The effect of mutants of the ER$_{del}$ type that destroy the functions of the ER ligand binding domain are similar to that of the ER$_{val}$ mutations, except that they will be more severe since such receptors completely lack repressor functions in the presence and absence of E$_2$. Our data point to a new mechanism by which nuclear receptors, through loss of repressor function can contribute to malignant development. Thus, some nuclear receptors can in their natural state have antioncogene roles such as the retinoblastoma gene product[18,19].

The following examples are intended to illustrate, but not limit, the invention.

EXAMPLE I

Estrogen Receptor is a Constitutive Transcriptional Activator and a Repressor

Characteristics of wild type and mutant ERs

To investigate the transcriptional regulatory properties of the human estrogen receptor, transient cotransfection experiments were carried out in which CV-1 cells were transfected with an estrogen receptor (ER) expression vector and an estrogen responsive CAT (chloramphenicol acetyl-transferase) reporter gene. We investigated the "wild type" receptor[9] that carries a GLY at position 400 (ER) and a mutant receptor that contains a VAL at position 400 (ER$_{val}$). This mutant receptor was cloned from a human mammary carcinoma cell line cDNA library and was originally thought to represent the wild type hER[10,11]. In addition we investigated another mutant receptor that we obtained by deleting the coding sequences for amino acids 442–498 (ER$_{del}$) of the hormone binding domain. The estrogen response element (ERE) we use here is a palindromic sequence (TCAGGTCACTGTGACCTGA) that is derived from the vitellogenin gene promoter[12].

The transient transfection was performed as follows. $1.7 \times 10^{-6}$ CV-1 cells were cultured in phenol-red free DME medium supplemented with 10% FCS that had been treated twice with charcoal. After 24 h cultures were washed with PBS and new medium was added. A modified calcium phosphate precipitation procedure was used for transient transfection[20]. 18 h after transfections, cultures were washed twice with PBS, and fresh medium was added together with the desired amount of hormone. After 24 h. cells were collected and cell extract was prepared. β-gal assay was performed as described[21]. CAT activity was assayed by using $^3$H-acetylated chloramphenicol and a mixed-phase scintillation measurement, as described in reference 22, below. CPM corrected for β-gal activity represents relative CAT activity. ERE-CAT was constructed by inserting the above synthetic ERE-oligonucleotide with BglII linkers into the BamH1 site of pBLCAT2[23].

In the absence of ligand, ER imparts a considerable constitutive transcriptional activity that can be further induced by estradiol (E$_2$). The ER$_{val}$ behaves like a classical, ligand dependent transcriptional activator, ER$_{del}$ is completely inactive (FIG. 1a). To demonstrate that the constitutive hormone independent enhancing activity of ER is not due to over expression of ER, we compared both basal level and ligand induced enhancer activity at different ER to ERE reporter gene ratios (FIG. 1b). We find that the constitutive activity of ER can be observed even at very low receptor concentrations (10 ng) where ERE is in large excess. Under those conditions E$_2$ dependent gene activation is also reduced (FIG. 1b). However, the constitutive ER activity is highest when saturating amounts of ER are present. Essentially the same results were obtained from transient transfections into F9 and Hela cells.

To investigate the ER protein-DNA interaction gel retardation assays were performed[5,13]. Receptor proteins were synthesized by in vitro transcription/translation[5,7], incubated with $^{32}$P-labelled ERE, and run on a non-denaturing acrylamide gel (FIG. 2a). The assay was performed as follows. ER and ER$_{val}$ cDNA cloned in Bluescript (Stratagene) were transcribed using T7 or T3 RNA polymerase, and translated, using rabbit reticulocyte translation system (Promega) as described[5]. 5 μl of in vitro translated receptor protein were incubated with $^{32}$P labeled ERE fragment in a reaction mixture containing 20 mM Hepes buffer pH 7.9, 50 mM KCl, 1 mM DTT, 2.5 mM MgCl$_2$, 10% glycerol, and 1 μg poly (dI-dC) at 25° C. for 20 min. Reaction mixtures were loaded on a 5% non-denaturing polyacrylamide gel containing 10 mM HEPES pH 7.9 and 3.3 mM sodium acetate pH 7.9, and electrophoresed. Gels were run at 4° C., 140 V for 3 h with continued circulation of buffer.

Again we observe that the various ER forms behave differently. ER binds to ERE strongly in the presence and absence of E$_2$. In contrast the mutant receptor ER$_{val}$ binds only weakly to the ERE in the absence of E$_2$ but binds strongly to ERE when E$_2$ is included in the reaction mixture. ER$_{del}$ binds poorly to the ERE in both the absence and presence of ligand (FIG. 2a). The observed DNA binding is specific as the labelled ERE can be competed by an excess of non-labelled ERE but not by an excess of nonspecific DNA (FIG. 2a). These gel retardation results correlate well with the transcriptional activation characteristics of the ERs. ER binds strongly to the ERE in the absence and presence of agonist and functions as a transcriptional activator in the presence and absence of $E_2$. $ER_{val}$ requires $E_2$ for both optimal DNA binding and transcriptional activation. The deleted receptor binds poorly to DNA in the presence and absence of $E_2$ and cannot be turned into a transcriptional activator by $E_2$.

To gain a more complete insight into how $E_2$ effects ER and $ER_{val}$ transcriptional activation, induction curves were carried out with both receptors using the transient cotransfection assay (FIG. 1c,d). We observe that ER shows already a clear response to $E_2$ at concentrations below $10^{-10}$M. Complete induction is observed at $10^{-9}$M $E_2$. This is consistent with the reported binding constant of ER for $E_2$[14]. The obvious responsiveness of ER to very low concentrations of $E_2$ in the transient transfection assay demonstrates that the observed high basal level activity of ER is not due to traces of estrogen-like activity present in the medium (the medium used throughout these experiments is phenol red-free and contains 2x charcoal stripped fetal calf serum (FCS)). The $ER_{val}$ is less sensitive to $E_2$ and shows an initial response to $E_2$ only at $10^{-9}$M and a complete induction at $10^{-7}$M of $E_2$. These data are consistent with the lower affinity of the $ER_{val}$ for $E_2$ if compared to $ER$[9].

Tamoxifen affects transcriptional activation and DNA binding of ERs

Figure 2B:
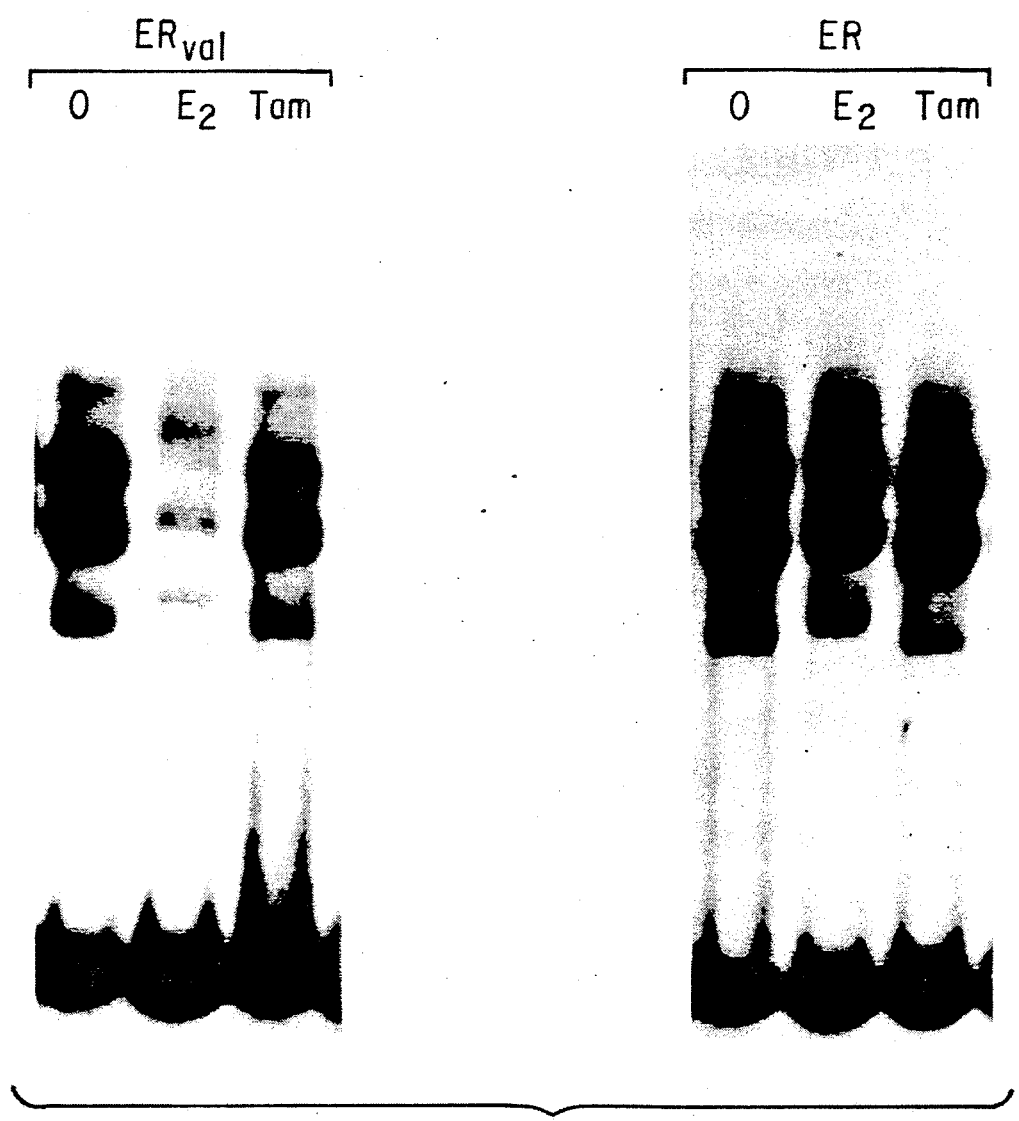

The antiestrogens tamoxifen (Tam) and 4-hydroxytamoxifen (OH-Tam) are known to affect estrogen receptor activity and are important therapeutic agents[14,15]. We therefore, investigated their effect on DNA binding and transcriptional activation. Tam and OH-Tam at high concentrations drastically increase the binding of $ER_{val}$ to the ERE (FIG. 2b). The binding of ER is equally strong in the absence and presence of Tam (FIG. 2b). The transcriptional enhancing activity of ER is maintained at the constitutive basal level in the presence of $10^{-8}$M OH-Tam. Higher concentrations of OH-Tam and Tam also do not significantly repress the ER basal level activity (FIG. 3a). Unexpectedly, OH-Tam increases the basal level activity of ER when the receptor is present in very low concentrations (FIG. 1b). The activation capacity of $ER_{val}$ is increased by OH-Tam ($10^{-8}$M) to the basal level of ER wild type (FIG. 3a). Our data show that the estrogen antagonists restore the DNA binding and basal level activity of the $ER_{val}$. Thus, agonists and antagonists appear to stabilize the DNA binding and gene activation functions of the mutant receptor $ER_{val}$. This is consistent with other binding studies on this receptor[16]. We also investigated the effects of OH-Tam on the $ER_{val}$ in the presence of $E_2$ ($10^{-8}$M). Under these conditions the $ER_{val}$ activation capacity is also reduced to the wild type basal level (FIG. 3a).

Figure 3C:
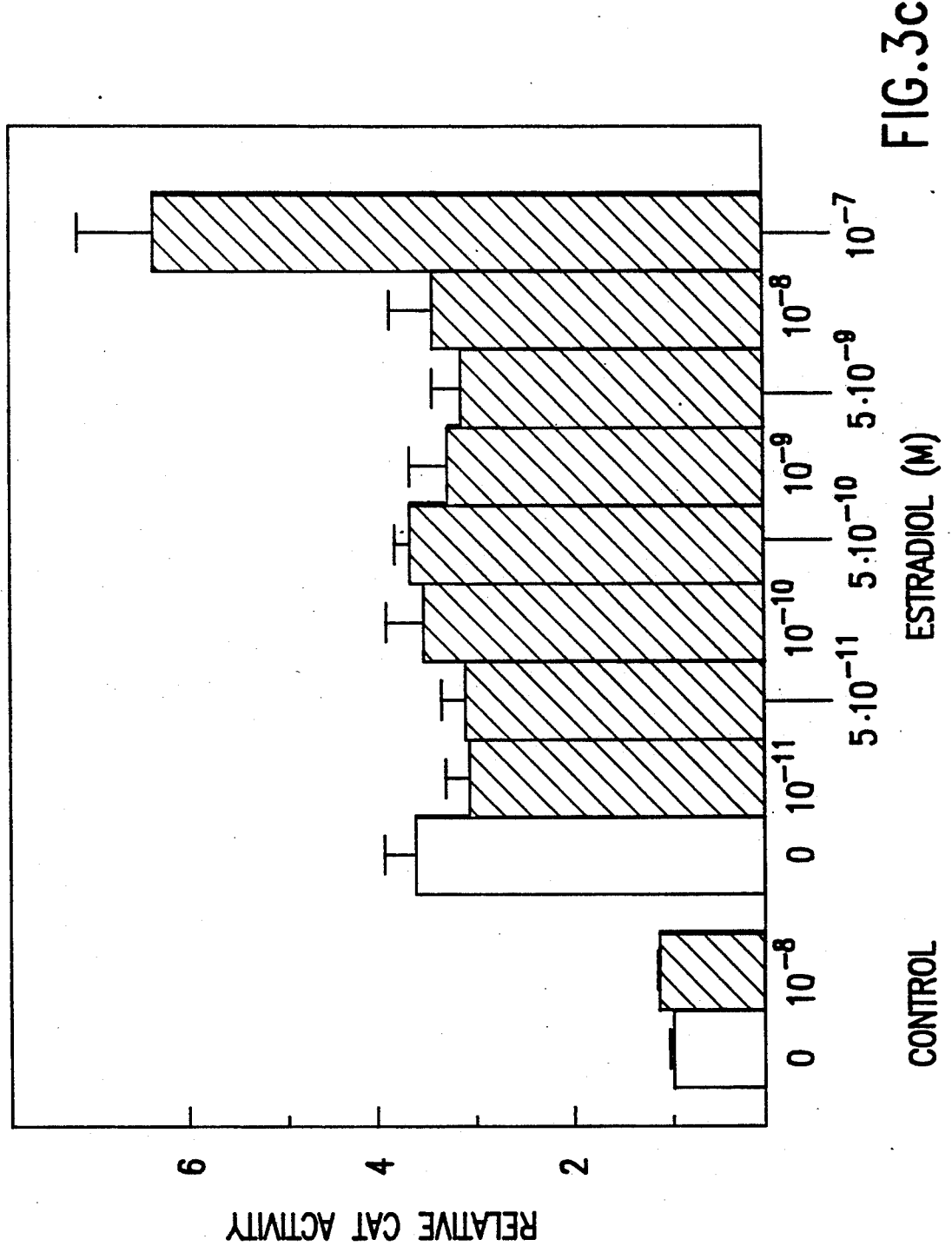

To analyze the antagonist effect on the wild type receptor function in more detail, hormonal induction at various $E_2$ concentration was measured in the presence of constant amounts of OH-Tam. At $10^{-9}$M OH-Tam, a first effect of $E_2$ is observed at $10^{-8}$M (FIG. 3b), whereas in the presence of $10^{-8}$M OH-Tam, $10^{-7}$M $E_2$ is needed for induction (FIG. 3c). Thus, nanomolar concentrations of OH-Tam are sufficient to repress $E_2$ action. In neither case is the high basal level of ER reduced. These experiments therefore also support our finding that the high basal level enhancing activity of ER is an intrinsic property of the wild type human ER and is not due to the presence of low concentrations of estrogen-like activity in the growth medium.

Figure 4B:
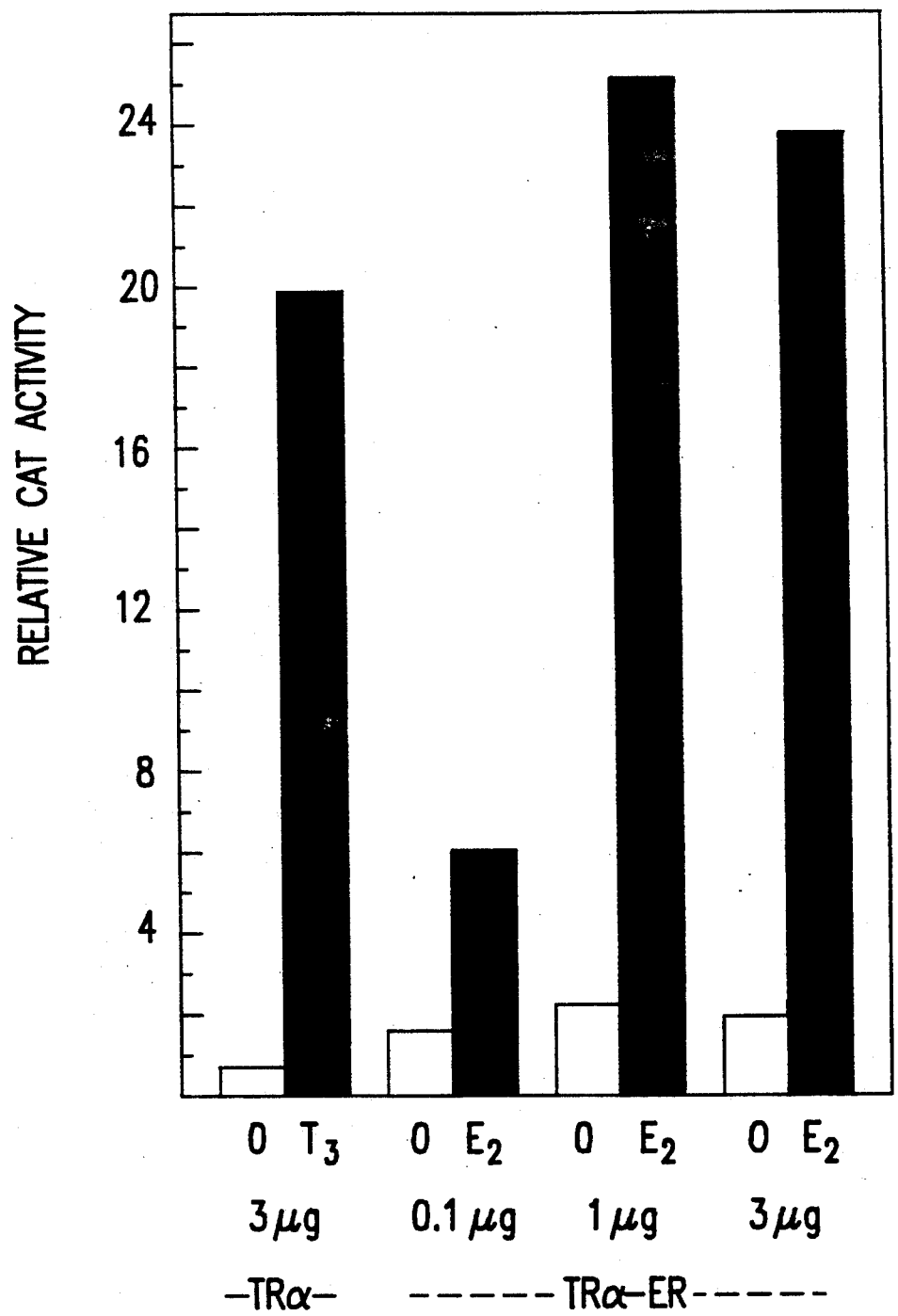
Figure 4C:
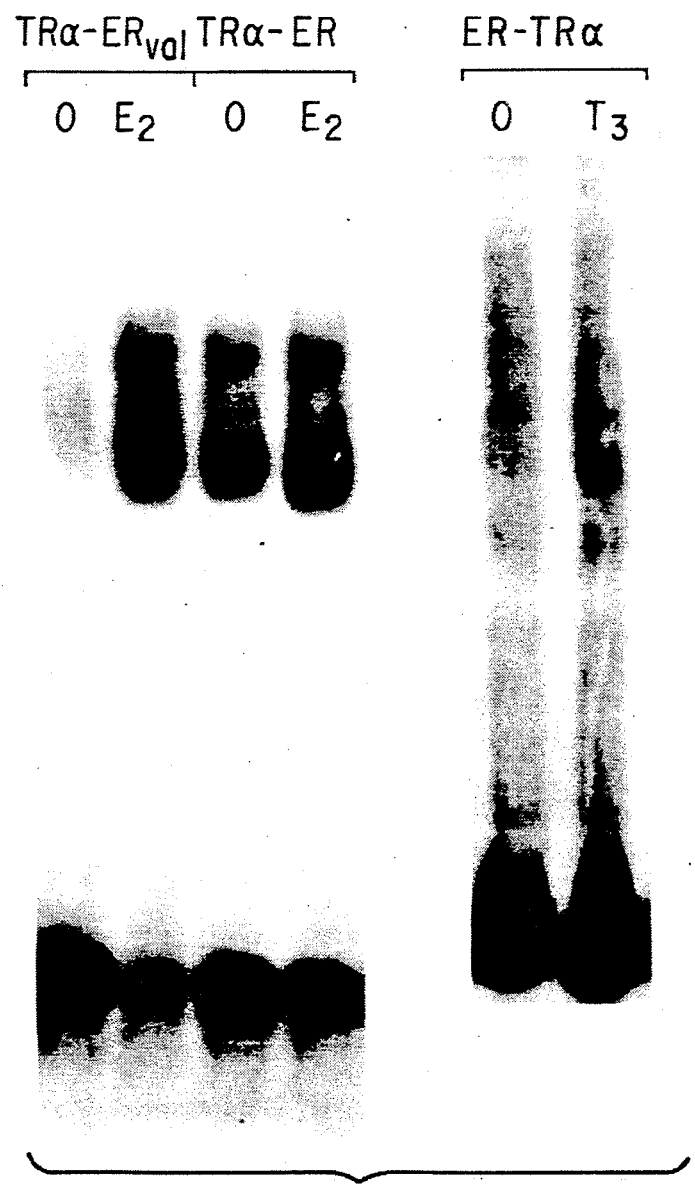

DNA binding and gene activation capacity are intrinsic properties of the ligand binding domain To determine the influence of individual domains on DNA binding and gene activation of ER, the hybrid receptors TRα-ER, TRα-$ER_{val}$ and ER-TRα (shown in FIG. 4a) were constructed. The transient transfection assay was used to determine basal and ligand induced gene activation by the hybrid receptor. In FIG. 4b the gene activation by TRα-ER is compared with TRα using a TRE reporter gene. The ER ligand binding domain confers increased basal level activity to TRα-ER. In the gel retardation assay TRα-$ER_{val}$ binds weakly to the TRE. The presence of $E_2$ increases the affinity of TRα-$ER_{val}$ for DNA several fold (FIG. 4c). TRα-ER binds strongly to the TRE in the absence and presence of ligand. ER-TRα binds weakly to the ERE in the presence and absence of hormone (FIG. 4c). Consequently, our data show that the ligand binding domains of $ER_{val}$ and ER wild type have intrinsic characteristics that determine the DNA binding properties and transcriptional activation properties of the receptors.

The ER is a ERE specific repressor

The strong interaction of ER with the ERE can have additional significance and could allow the ER to function simultaneously as a transcriptional repressor and activator, i.e., the ER can enhance to a defined constitutive or induced level and simultaneously prevent other transcriptional activators with overlapping DNA specificity from further inducing the ERE.

To analyze the repressor functions of ER we chose a potent $E_2$ independent activator of the ERE: the hybrid receptor ER-TRα. In the presence of $T_3$, ER-TRα alone efficiently enhances ERE-CAT gene expression (FIG. 5). However, when ER and ER-TRα were cotransfected into the same cells, strong repression of ER-TRα activity is observed. OH-Tam slightly increases the repression capacity of ER (FIG. 5). $ER_{val}$ is only an efficient repressor of ER-TRα in the presence of OH-Tam (FIG. 5). This demonstrates that strong interaction with the specific DNA site is necessary for the repressor action as observed for ER in the presence and absence of OH-Tam and for the $ER_{val}$ in the presence of OH-Tam (FIG. 2b).

Dissociation kinetics of the ER-DNA complex

The gel retardation data shown in FIG. 2 do not allow us to distinguish whether different ER-DNA complexes are formed in the absence of ligand or in the presence of agonist or antagonist. To measure the stability of the ER-ERE complexes in the presence and absence of ligands, the dissociation of the complexes was analyzed (FIG. 6). We observe no substantial difference in the dissociation of the ER-DNA complex in the presence and absence of $E_2$ or OH-Tam. This may indicate that agonist- and antagonist-ER complex bind to DNA identically or in very similar conformations. In the case of the $ER_{val}$-DNA complex, we also did not observe any difference between the half lives measured in the presence of agonists or antagonists, however, in the absence of ligand the complex was very unstable.

Although the invention has been described with reference to the presently preferred embodiment, it should

REFERENCES

1. Guiochon-Mantel, A., Loosfelt, H., Lescop, P., Sar, S., Atger, M., Perrot-Applanat, M., and Milgrom, E. *Cell* 57, 1147–1154 (1989).
2. King, W. J., and Greene, G. L. *Nature* 307, 745–747 (1984).
3. Welshons, W. V., Krummer, B. M., and Gorski, J. *Endocrinology* 117, 2140–2147 (1985).
4. Picard, D., and Yamamoto, K. R. *EMBO J.* 6, 3333–3340 (1987).
5. Graupner, G., Wills, K. N., Tzukerman, M., Zhang, X-k., and Pfahl, M. *Nature* 340, 653–656 (1989).
6. Krust, A., Green, S., Argos, P., Kumar, V., Walter, P., Bornet, J.-M., and Chambon, P. *EMBO J.* 5, 891–897 (1986).
7. Benbrook, D., Lernhardt, E., and Pfahl, M. *Nature* 333, 669–672 (1988).
8. Umesono, K., and Evans, R. M. *Cell* 57, 1139–1146 (1989).
9. Tora, L., Mullick, A., Metzger, D., Ponglinkitmongkol, M., Park, I., and Chambon, P. *EMBO J.* 8, 1981–1986 (1989).
10. Green, G. L., Gilna, P. L., Waterfield, M. et al. *Science* 231, 1150–1154 (1986).
11. Green, S., Walter, P., Kumar, V. et al. *Nature* 320, 134–139 (1986).
12. Klein-Hitpass, L., Schorpp, M., Wagner, U. and Ryffel, G. U. *Cell* 46, 1053–1061 (1986).
13. Garner, M. M., and Revzin, A. *Nucl. Acids Res.* 9, 3047–3060 (1981).
14. Jensen, E. V., Green, G. L., Closs, L. E., DeSombre, E. R., and Nadji, M. in *Recent Progress in Hormone Research*, ed. Greep, R. O. (Academic, New York), 38, 1–34 (1982).
15. Henderson, I. C., and Canellos, G. P. *New Engl. J. Med.* 302, 78–90 (1980).
16. Kumar, V., and Chambon, P. *Cell* 55, 145–156 (1988).
17. Seibert, K., Shafie, S. M., Triche, T. J., Whang-Peng, J. J., O'Brien, S. J., Toney, J. H., Huff, K. K., and Lippman, M. E. *Cancer Res.* 43, 2223–2239 (1983).
18. Horowitz, J. M., Yandell, D. W., Park, S.-H., Canning, S., Whyte, P., Buchkovich, K., Harlow, E., Weinberg, R. A., and Dryja, T. P. *Science* 243, 940–943 (1989).
19. Bookstein, R., Lee, E., Y.-H., To, H., Young, L.-J., Sery, T. W., Hayes, R. C., Friedmann, T., and Lee, W.-H. *Proc. Natl. Acad. Sci. USA* 85, 2210–2214 (1988).
20. Chen, C. A., and Okayama, H. *BioTechniques* 6, 632–637 (1988).
21. Rosenthal, N. *Methods Enzymol.* 152, 704–720 (1987).
22. Nielsen, D. A., Chang, T-C., and Shapiro, D. J. *Anal. Biochem.* 179, 19–23 (1989).
23. Lucknow, B., and Schutz, G. *Nucl. Acids Res.* 15, 5490 (1987).

What is claimed is:

1. A method of comparatively determining the ability of a ligand to effect the constitutive activator or repressor activity of an estrogen receptor which has the constitutive activator or repressor activity and a estrogen receptor which lacks the constitutive activator or repressor activity comprising separately binding the ligand to the estrogen receptor which has the constitutive activator or repressor activity and the estrogen receptor which lacks the constitutive activator or repressor activity, determining the effect of the ligand on the activity of the estrogen receptor which has the constitutive activator or repressor activity and the estrogen receptor which lacks the constitutive activator or repressor activity, and comparing the activity.

2. The method of claim 1, wherein comparing the effect of the ligand on the constitutive activator or repressor activity is determined by a gel retardation assay.

3. The method of claim 1, wherein comparing the effect of the ligand on the constitutive activator or repressor activity is determined by transient transfection.

4. A method of selecting a ligand which increases or decreases the basal level transcription or repressor activity of a estrogen receptor which lacks the constitutive activator or repressor activity comprising the steps of contacting the ligand with the estrogen receptor which lacks the constitutive activator or repressor activity, determining the effect of the ligand on basal level transcription, and selecting those ligands which either increase or decrease the basal level transcription.

5. A method of selecting a ligand for increasing or decreasing the constitutive activator or repressor activity of a estrogen receptor which lacks the constitutive activator or repressor activity compared to estrogen receptor which has the constitutive activator or repressor activity comprising the steps of separately contacting the estrogen receptor which lacks the constitutive activator or repressor activity and the estrogen receptor which has the constitutive activator or repressor activity with the ligand in separate reactions, comparing the effect of the ligand on the activity of the estrogen receptor which lacks the constitutive activator or repressor activity and the estrogen receptor which has the constitutive activator or repressor activity, and selecting those ligands which increase or decrease the activity of the estrogen receptor which lacks the constitutive activator or repressor activity more than the activity of the estrogen receptor which has the constitutive activator or repressor activity.

6. A method of diagnosing or predicting the predisposition of an individual to a pathology, associated with the constitutive activator or repressor activity of estrogen receptor, in an individual comprising detecting an estrogen receptor which lacks the constitutive activator or repressor activity, the presence of an estrogen receptor which lacks the constitutive activator or repressor activity indicating the pathology or a predisposition to the pathology.

7. The method of claim 6, wherein the estrogen receptor which lacks the constitutive activator or repressor activity is detected by the presence of altered restriction sites at the site of the mutation.

8. The method of claim 6, wherein the estrogen receptor which lacks the constitutive activator or repressor activity is characterized by an non-Gly residue at position 400.

9. The method of claim 8, wherein the non-Gly residue is Val or Met.

10. The method of claim 6, wherein the estrogen receptor which lacks the constitutive activator or repressor activity is characterized by altered activity of the ligand binding domain as measured by DNA binding and ligand binding activities.

11. The method of claim 10, wherein the estrogen receptor which lacks the constitutive activator or repressor activity is characterized by a deletion in the ligand binding domain.

12. The method of claim 6, wherein the estrogen receptor which lacks the constitutive activator or repressor activity is detected by contacting a nucleotide probe, having a sequence selectively complementary to the nucleotide sequence of the estrogen receptor which lacks the constitutive activator or repressor activity, with a nucleic acid containing sample from the individual under conditions such that substantially only nucleotide sequences of the estrogen receptor which lacks the constitutive activator or repressor activity will hybridize with the probe, and detecting the nucleic acids which hybridize, thereby detecting a estrogen receptor which lacks the constitutive activator or repressor activity.

13. The method of claim 12, further comprising the step of amplifying a portion of the nucleic acid containing the mutation prior to contacting the nucleotide probe.

14. The method of claim 6, wherein the pathology results from a defect in the repressor activity of the estrogen receptor.

15. The method of claim 14, wherein the pathology is a cancer.

16. The method of claim 6, wherein the pathology results from a defect in the basal level transcription activity of the estrogen receptor.

17. The method of claim 16, wherein the pathology is osteoporosis.

* * * * *